US012766272B2

(12) United States Patent
Zhang et al.

(10) Patent No.: US 12,766,272 B2
(45) Date of Patent: Oct. 20, 2026

(54) ELECTRONIC VAPORIZATION DEVICE

(71) Applicant: SHENZHEN SMOORE TECHNOLOGY LIMITED, Shenzhen (CN)

(72) Inventors: Xieen Zhang, Shenzhen (CN); Shiyi Cheng, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 662 days.

(21) Appl. No.: 18/334,263

(22) Filed: Jun. 13, 2023

(65) Prior Publication Data

US 2023/0321364 A1 Oct. 12, 2023

Related U.S. Application Data

(63) Continuation of application No. PCT/CN2020/137571, filed on Dec. 18, 2020.

(51) Int. Cl.
*A61M 11/00* (2006.01)

(52) U.S. Cl.
CPC ......... *A61M 11/001* (2014.02); *A61M 11/007* (2014.02)

(58) Field of Classification Search
CPC .............. A61M 11/001; A61M 11/007; A61M 11/005; A61M 15/0085; A61M 2205/0211; A61M 2205/0294; A61M 11/003; A24F 40/05; A24F 40/10; B05B 12/08; B05B 17/0676; B05B 17/0646
See application file for complete search history.

(56) References Cited

U.S. PATENT DOCUMENTS

| | | | | |
|---|---|---|---|---|
| 5,435,282 | A | 7/1995 | Haber et al. | |
| 7,628,339 | B2 * | 12/2009 | Ivri | B05B 17/0646 239/338 |
| 10,624,391 | B2 | 4/2020 | Chen | |
| 10,779,576 | B2 | 9/2020 | Verleur et al. | |
| 2011/0168172 | A1 | 7/2011 | Patton et al. | |

(Continued)

FOREIGN PATENT DOCUMENTS

| | | | |
|---|---|---|---|
| CN | 102896062 | A | 1/2013 |
| CN | 102905748 | A | 1/2013 |
| CN | 105664311 | A | 6/2016 |

(Continued)

OTHER PUBLICATIONS

Translation of DE-102005052898-A1 (Year: 2007).*

(Continued)

*Primary Examiner* — Victoria Murphy
(74) *Attorney, Agent, or Firm* — Leydig, Voit & Mayer, Ltd.

(57) ABSTRACT

An electronic vaporization device includes: a microporous atomizing sheet; and a needle tube, one end of the needle tube being spaced apart from the microporous atomizing sheet, and an other end of the needle tube being for insertion into a liquid storage assembly, the needle tube being conveying liquid in the liquid storage assembly to the microporous atomizing sheet to form to-be-vaporized liquid, the to-be-vaporized being adsorbed between the microporous atomizing sheet and the needle tube through surface tension.

17 Claims, 8 Drawing Sheets

(56) References Cited

U.S. PATENT DOCUMENTS

| | | | | |
|---|---|---|---|---|
| 2019/0366023 | A1* | 12/2019 | Alizoti | A61M 16/208 |
| 2020/0197631 | A1* | 6/2020 | Stedman | A61M 11/007 |

FOREIGN PATENT DOCUMENTS

| | | | | |
|---|---|---|---|---|
| CN | 106422005 | A | 2/2017 | |
| CN | 206261814 | U | 6/2017 | |
| CN | 107970505 | A | 5/2018 | |
| CN | 109568738 | A | 4/2019 | |
| CN | 109640711 | A | 4/2019 | |
| CN | 208710699 | U | 4/2019 | |
| CN | 209519196 | U | 10/2019 | |
| CN | 110420369 | A | 11/2019 | |
| CN | 111744081 | A | 10/2020 | |
| CN | 211678341 | U | 10/2020 | |
| CN | 107970505 | B | 11/2020 | |
| CN | 111888592 | A | 11/2020 | |
| DE | 102005052898 | A1 * | 5/2007 | B05B 11/1001 |
| JP | 2008168222 | A | 7/2008 | |
| WO | 2018172561 | A1 | 9/2018 | |
| WO | 2020227717 | A1 | 11/2020 | |

OTHER PUBLICATIONS

European Patent Office, Search Report in European Patent Application No. 20965605.7 (Jul. 29, 2024).

Patent Cooperation Treaty, International Search Report and Written Opinion, International Application No. PCT/CN2020/137571 (Sep. 23, 2021).

Chinese Patent Office, Office Action in Chinese Patent Application No. 202011503451.9 (Apr. 21, 2023).

Chinese Patent Office, Notice of Registration and Notification to Grant Patent Right in Chinese Patent Application No. 202011509253.3 (Apr. 26, 2023).

* cited by examiner

ELECTRONIC VAPORIZATION DEVICE

CROSS-REFERENCE TO PRIOR APPLICATION

This application is a continuation of International Patent Application No. PCT/CN2020/137571, filed on Dec. 18, 2020. The entire disclosure is hereby incorporated by reference herein.

FIELD

This application relates to the field of vaporizer technologies, and specifically, to an electronic vaporization device.

BACKGROUND

In the treatment of respiratory system diseases, a vaporization inhalation therapy is an important and effective treatment. The vaporization inhalation therapy is to vaporize medicinal liquid into tiny droplets by using a vaporizer. Patients inhale the medicinal liquid into the respiratory tracts and the lungs through breathing, and the medicinal liquid is deposited in the respiratory tracts or the lungs, so as to achieve the purpose of painless, rapid and effective treatment.

After being used by the patients, the conventional vaporizer usually does not stop working until the medicinal liquid in the vaporizer is consumed, a vaporized dose of the medicinal liquid cannot be precisely controlled, and it is easy for the patients to inhale an excessive dose of the medicinal liquid or an insufficient dose of the medicinal liquid. As a result, an expected treatment effect cannot be achieved.

SUMMARY

In an embodiment, the present invention provides an electronic vaporization device, comprising: a microporous atomizing sheet; and a needle tube, one end of the needle tube being spaced apart from the microporous atomizing sheet, and an other end of the needle tube being configured for insertion into a liquid storage assembly, the needle tube being configured to convey liquid in the liquid storage assembly to the microporous atomizing sheet to form to-be-vaporized liquid, the to-be-vaporized being adsorbed between the microporous atomizing sheet and the needle tube through surface tension.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
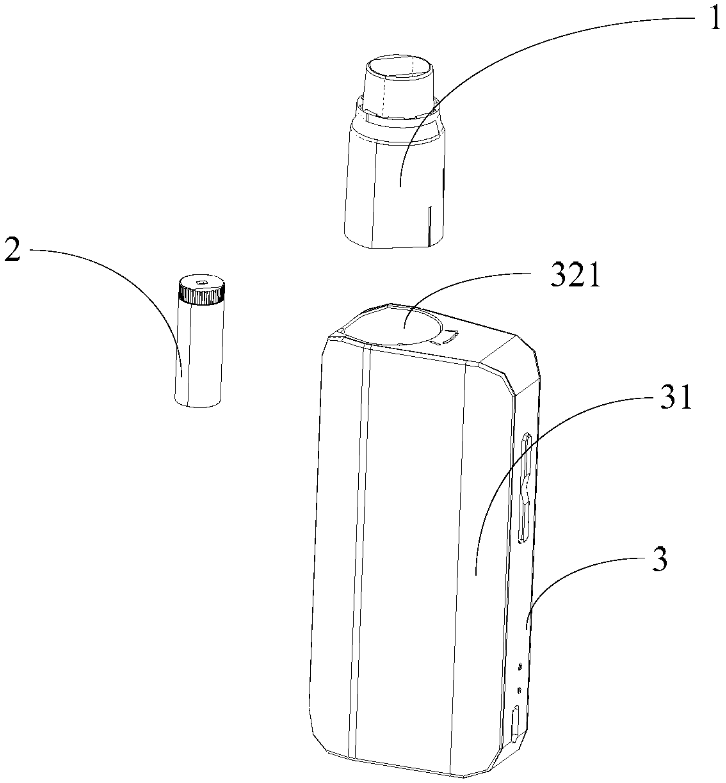
FIG. 1 is a schematic structural diagram of an electronic vaporization device according to this application.

In an embodiment, the present invention provides an electronic vaporization device, to resolve the technical problem that a vaporized dose of medicinal liquid cannot be precisely controlled in the related art.

In an embodiment, the present invention provides an electronic vaporization device, including a microporous atomizing sheet and a needle tube, where one end of the needle tube is spaced apart from the microporous atomizing sheet, and the other end of the needle tube is configured for insertion into a liquid storage assembly; the needle tube is configured to convey liquid in the liquid storage assembly to the microporous atomizing sheet to form to-be-vaporized liquid; and the to-be-vaporized liquid is adsorbed between the microporous atomizing sheet and the needle tube through surface tension.

The electronic vaporization device further includes a vaporization base, where the microporous atomizing sheet is arranged on one end of the vaporization base and is engaged with an end portion of the vaporization base to form a vaporization chamber; and the needle tube is fixed to the vaporization base.

The microporous atomizing sheet includes a microporous region, both the cross section of the vaporization chamber and the microporous region are circular, and the vaporization chamber, the microporous region of the microporous atomizing sheet, and the needle tube are coaxially arranged.

The diameter of the vaporization chamber is greater than the diameter of the microporous region and is less than the doubled diameter of the microporous region.

The diameter of the vaporization chamber ranges from 4 mm to 5 mm; and a distance between the end of the needle tube close to the microporous atomizing sheet and the side wall of the vaporization chamber ranges from 1.2 mm to 1.8 mm.

A distance between the end of the needle tube close to the microporous atomizing sheet and the microporous atomizing sheet ranges from 0.2 mm to 0.4 mm.

The end of the vaporization base close to the microporous atomizing sheet is provided with an annular groove, and a seal member is arranged in the annular groove; and a non-microporous region of the microporous atomizing sheet covers the annular groove.

The annular groove is circular ring-shaped, the seal member is a circular ring, and the seal member is made of silicone.

The end of the vaporization base close to the microporous atomizing sheet is provided with an opening, the annular groove is provided around the opening, the microporous atomizing sheet covers the opening and is engaged with the opening to form the vaporization chamber, and the end of the needle tube close to the microporous atomizing sheet is spaced apart from the side wall of the opening.

The opening is a through hole or a blind hole.

The end of the needle tube close to the microporous atomizing sheet is provided with a tube cover, and the tube cover is configured to increase adhesion of the to-be-vaporized liquid.

The outer wall of the tube cover is spaced apart from the side wall of the vaporization chamber, and the tube cover is made of silicone.

The needle tube is a hollow cylindrical metal tube, and the inner diameter of the needle tube ranges from 0.7 mm to 1.0 mm.

The electronic vaporization device further includes a controller, where a conductor is arranged on the needle tube, and the conductor is electrically connected to the controller; the microporous atomizing sheet is electrically connected to the controller, and the needle tube and the microporous atomizing sheet form an impedance sensor; and the controller detects a resistance value between the needle tube and the microporous atomizing sheet and controls an operating state of the microporous atomizing sheet according to a detection result.

The end portion of the vaporization base away from the microporous atomizing sheet is provided with an accommodating groove, the accommodating groove is configured to accommodate the liquid storage assembly, and the end of the needle tube away from the microporous atomizing sheet is arranged in the accommodating groove.

Beneficial effects of this application are as follows: Different from the related art, the electronic vaporization device in this application includes a microporous atomizing sheet and a needle tube, where one end of the needle tube is spaced apart from the microporous atomizing sheet, and the other end of the needle tube is configured for insertion into a liquid storage assembly; and the needle tube is configured to convey liquid in the liquid storage assembly to the microporous atomizing sheet to form to-be-vaporized liquid; and the microporous atomizing sheet is configured to vaporize the to-be-vaporized liquid, and the to-be-vaporized liquid is adsorbed between the microporous atomizing sheet and the needle tube through surface tension. Liquid in the liquid storage assembly is conveyed to the microporous atomizing sheet by using the needle tube, to precisely control a vaporized dose, which can prevent a patient from inhaling excessive medicinal liquid or insufficient medicinal liquid, thereby achieving an expected therapeutic effect for a vaporization inhalation therapy.

This application is further described in detail below with reference to the accompanying drawings and embodiments. It should be specifically noted that, the following embodiments are merely used for describing this application rather than limiting the scope of this application. Similarly, the following embodiments are merely some rather than all of the embodiments of this application, and all other embodiments obtained by a person of ordinary skill in the art without creative efforts shall fall within the protection scope of this application.

The terms “first”, “second”, and “third” in this application are merely intended for a purpose of description, and shall not be understood as indicating or implying an indication or implication of relative importance or implicitly indicating indication of the number of indicated technical features. Therefore, features defining “first”, “second”, and “third” can explicitly or implicitly include at least one of the features. In description of this application, “more” means at least two, such as two and three unless it is specifically defined otherwise. All directional indications (for example, up, down, left, right, front, back . . . ) in the embodiments of this application are only used for explaining relative position relationships, movement situations, or the like between the various components in a specific posture (as shown in the accompanying drawings). If the specific posture changes, the directional indications change accordingly. Terminologies “comprise”, “have”, and any variations thereof in the embodiments of this application are intended to indicate non-exclusive inclusion. For example, a process, method, system, product, or device that includes a series of steps or units is not limited to the listed steps or units, but further optionally includes a step or unit that is not listed, or further optionally includes another step or component that is intrinsic to the process, method, product, or device.

“Embodiment” mentioned in the specification means that particular features, structures, or characteristics described with reference to the embodiment may be included in at least one embodiment of this application. The term appearing at different positions of the specification may not refer to the same embodiment or an independent or alternative embodiment that is mutually exclusive with another embodiment. A person skilled in the art explicitly or implicitly understands that the embodiments described in the specification may be combined with other embodiments.

FIG. 1 is a schematic structural diagram of an electronic vaporization device according to this application.

The electronic vaporization device may be used for vaporization of liquid substrates such as medicinal liquid and is applied to medical equipment for treating diseases of upper and lower respiratory, to vaporize medical drugs. The electronic vaporization device includes a vaporization assembly 1, a liquid storage assembly 2, and a control assembly 3. During use, the vaporization assembly 1 and the liquid storage assembly 2 are mounted on the control assembly 3. The liquid storage assembly 2 is configured to store medicinal liquid. The vaporization assembly 1 is configured to vaporize the liquid in the liquid storage assembly 2. The control assembly 3 includes a controller 31 and a mounting cavity 321, the vaporization assembly 1 and the liquid storage assembly 2 are mounted in the mounting cavity 321, and the control assembly 3 is configured to convey the liquid in the liquid storage assembly 2 to the vaporization assembly 1 and control operation of the vaporization assembly 1.

The vaporization assembly 1, the liquid storage assembly 2, and the control assembly 3 may be integrally arranged or detachably connected, which are designed according to specific requirements.

Figure 2:
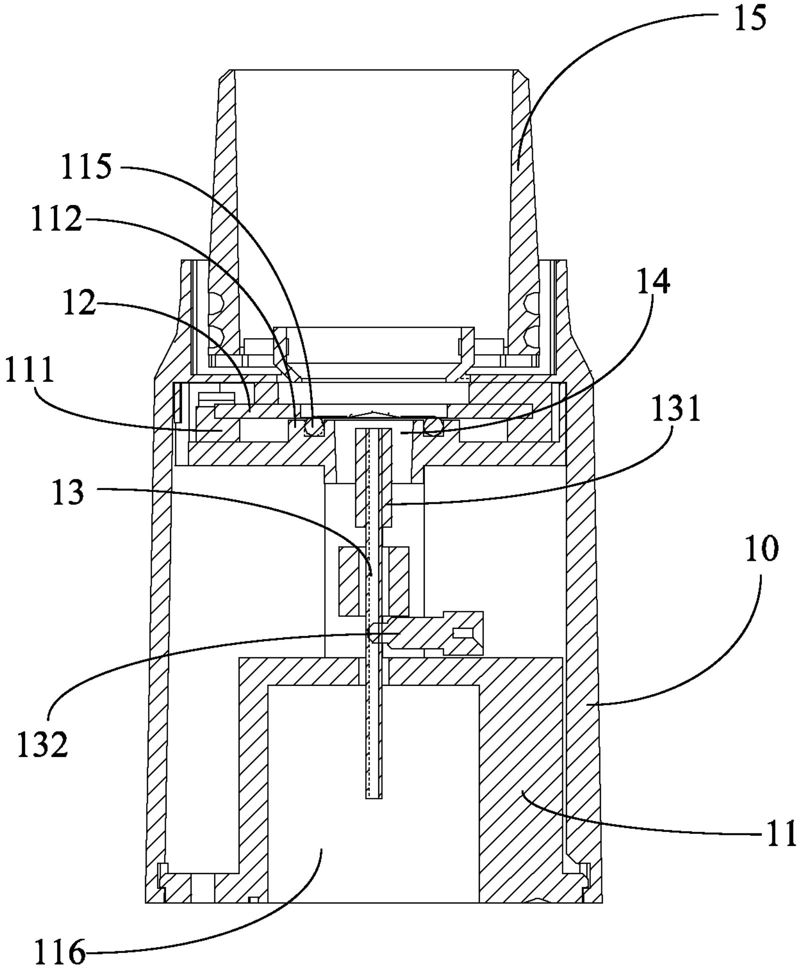
FIG. 2 is a schematic cross-sectional view of a vaporization assembly according to this application.

FIG. 2 is a schematic cross-sectional view of a vaporization assembly according to this application.

The vaporization assembly 1 includes a vaporization shell 10, a vaporization base 11, a microporous atomizing sheet 12, and a needle tube 13. The microporous atomizing sheet 12 is arranged on one end of the vaporization base 11 and is engaged with an end portion of the vaporization base 11 to form a vaporization chamber 14. An extending direction of the needle tube 13 is perpendicular to an extending direction of the microporous atomizing sheet 12. Another angle, for example, between 60 degrees and 90 degrees, may alternatively be formed between the extending direction of the needle tube 13 and the extending direction of the microporous atomizing sheet 12, which is designed as required. The needle tube 13 is fixed to the vaporization base 11. One end of the needle tube 13 is arranged in the vaporization chamber 14 and is spaced apart from the microporous atomizing sheet 12. During use, the other end of the needle tube 13 is inserted into the liquid storage assembly 2, to convey the liquid in the liquid storage assembly 2 to the microporous atomizing sheet 12 to form to-be-vaporized liquid. The microporous atomizing sheet 12 is configured to vaporize the to-be-vaporized liquid. The to-be-vaporized liquid is adsorbed between the microporous atomizing sheet 12 and the needle tube 13 through surface tension. A suction nozzle portion 15 is formed or arranged on one end of the vaporization shell 10, and the microporous atomizing sheet 12, the needle tube 13, and the vaporization base 11 are arranged in the vaporization shell 10 together. The suction nozzle portion 15 is in communication with the vaporization chamber 14 enclosed by the microporous atomizing sheet 12 and the vaporization base 11, and a user inhales, through the suction nozzle portion 15, medicinal liquid vaporized by the microporous atomizing sheet 12.

Figure 3:
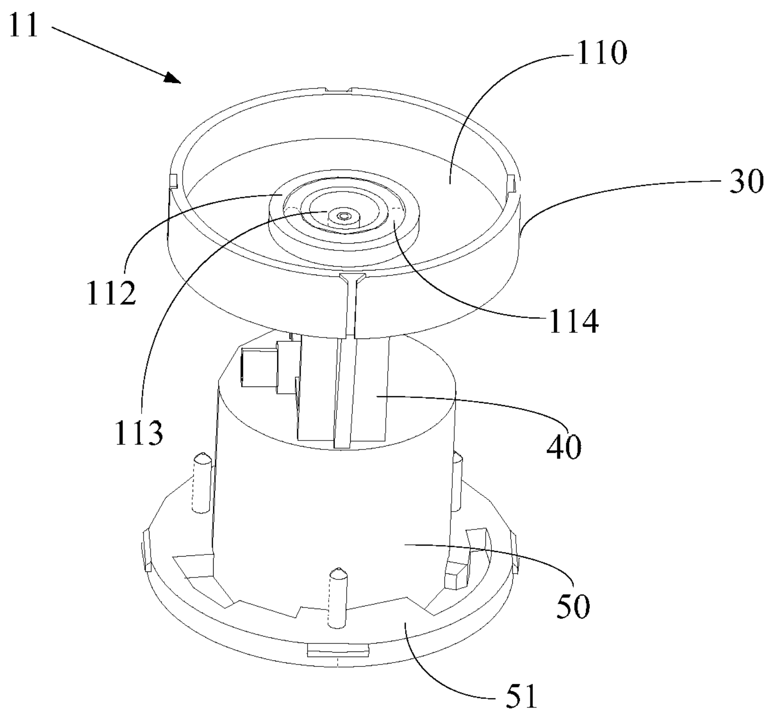
FIG. 3 is a three-dimensional structural diagram of a vaporization base in a vaporization assembly according to this application.
Figure 4:
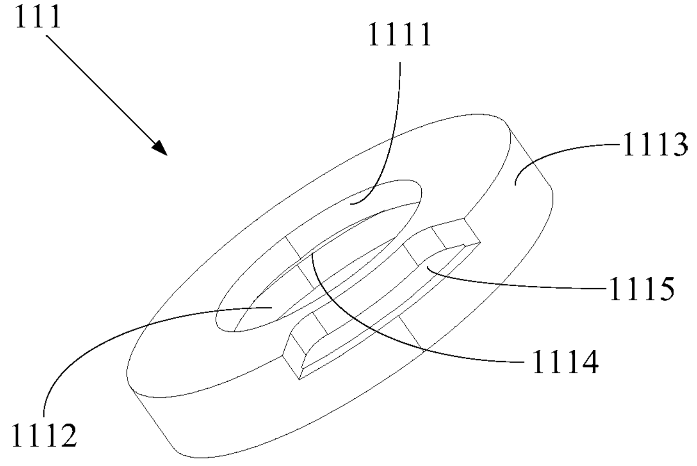
FIG. 4 is a three-dimensional structural diagram of a first seal member in a vaporization assembly according to this application.

FIG. 3 is a three-dimensional structural diagram of a vaporization base in a vaporization assembly according to this application. FIG. 4 is a three-dimensional structural diagram of a first seal member in a vaporization assembly according to this application.

A mounting groove 110 is provided on the end of the vaporization base 11, and the mounting groove 110 is configured to mount the microporous atomizing sheet 12. The shape of the mounting groove 110 matches the shape of the microporous atomizing sheet 12. A first seal member 111 is arranged on a periphery of the microporous atomizing sheet 12, and the microporous atomizing sheet 12 and the first seal member 111 are together arranged in the mounting groove 110. The first seal member 111 can fix the microporous atomizing sheet 12, to prevent the microporous atomizing sheet 12 from shaking on the end of the vaporization base 11 with affecting operation of the medicinal liquid vaporization process.

The microporous atomizing sheet 12 includes a piezoelectric ceramic plate, a metal baseplate, a first electrode, and a second electrode. The first electrode is electrically connected to the piezoelectric ceramic plate, the second electrode is electrically connected to the metal baseplate, and both the first electrode and the second electrode are electrically connected to the controller 31. The metal baseplate is a circular plate, the piezoelectric ceramic plate is a circular ring, and the diameter of the metal baseplate is greater than the inner diameter of the piezoelectric ceramic plate. A through hole is provided in a central region of the piezoelectric ceramic plate, and a region of the metal baseplate corresponding to the central region of the piezoelectric ceramic plate is provided with a plurality of micropores. That is, the microporous atomizing sheet 12 includes a microporous region, the microporous region is provided with a plurality of micropores, and the suction nozzle portion 15 is in communication with the vaporization chamber 14 by using the plurality of micropores. In this embodiment, the central region of the metal baseplate protrudes toward the suction nozzle portion 15, to provide a relatively large adhesion surface for the to-be-vaporized liquid, thereby increasing adhesion of the to-be-vaporized liquid. In another implementation, the metal baseplate may be a planar structure, which is selected as required. This is not limited in this application.

The first seal member 111 includes a first panel 1111, a second panel 1112, and a side wall 1113. The first panel 1111 is arranged opposite to the second panel 1112. The first panel 1111 is arranged on one end of the side wall 1113, and the second panel 1112 is arranged on the other end of the side wall 1113. That is, the first panel 1111 and the second panel 1112 are arranged at an interval on the side wall 1113, and the side wall 1113 connects the first panel 1111 and the second panel 1112. In an embodiment, the side wall 1113 connects the edge of the first panel 1111 and the edge of the second panel 1112 to form an integral structure. Preferably, the first panel 1111, the second panel 1112, and the side wall 1113 are integrally formed. The first seal member 111 is made of rubber, silicone, or the like.

The first panel 1111 is arranged on a side of the second panel 1112 close to the suction nozzle portion 15. All the first panel 1111, the second panel 1112, and the side wall 1113 are circular ring structures. The outer diameter of the first panel 1111 is the same as the outer diameter of the second panel 1112. The inner diameter of the first panel 1111 may be the same as or different from the inner diameter of the second panel 1112, which is designed as required. The inner diameter of the side wall 1113 is the same as the outer diameter of the first panel 1111 and the outer diameter of the second panel 1112. The thickness of the first panel 1111 is the same as the thickness of the second panel 1112, and a difference between the outer diameter and the inner diameter of the side wall 1113 is the same as the thickness of the first panel 1111 and the thickness of the second panel 1112.

The first panel 1111, the second panel 1112, and the side wall 1113 together enclose an atomizing sheet cavity 1114 for accommodating the microporous atomizing sheet 12. That is, the microporous atomizing sheet 12 is located between the first panel 1111 and the second panel 1112 and is not located beyond the region enclosed by the side wall 1113. A center through hole of the first panel 1111 is in communication with a center through hole of the second panel 1112 and can expose the microporous region on the microporous atomizing sheet 12. In an embodiment, the first panel 1111 and the second panel 1112 are coaxially arranged, and the inner diameter of the first panel 1111 is greater than the inner diameter of the second panel 1112.

An opening 1115 is provided on the first seal member 111, to facilitate mounting of the microporous atomizing sheet 12 into the atomizing sheet cavity 1114. In this embodiment, the opening 1115 is provided at a joint of the side wall 1113 and the first panel 1111, that is, the opening 1115 is formed by cutting off a piece of the edge of the first seal member 111. The opening 1115 may alternatively be provided on the side wall 1113, provided that the microporous atomizing sheet 12 can be mounted in the atomizing sheet cavity 1114, which is not limited in this application.

In another implementation, the microporous atomizing sheet 12 may alternatively be in another shape such as a square, the structure of the first seal member 111 matches that of the microporous atomizing sheet 12, and the shape of the mounting groove 110 matches that of the microporous atomizing sheet, which is selected as required.

Still referring to FIG. 3, a protrusion 112 is arranged on the bottom wall of the mounting groove 110, and the height of the protrusion 112 is the same as the thickness of the second panel 1112. The protrusion 112 is embedded in the central through hole of the second panel 1112. An opening 113 is provided on the protrusion 112, and the opening 113 corresponds to the microporous region of the microporous atomizing sheet 12. That is, the end of the vaporization base 11 close to the microporous atomizing sheet 12 is provided with the opening 113, the microporous atomizing sheet 12 covers the opening 113, the microporous region is suspended in the opening 113, and the microporous atomizing sheet 12 is engaged with the opening 113 to form the vaporization chamber 14. An annular groove 114 is provided around the opening 113 on the protrusion 112 for mounting a second seal member 115. The size of the annular groove 114 matches the size of the second seal member 115. That is, the end of the vaporization base 11 close to the microporous atomizing sheet 12 is provided with the annular groove 114, and the second seal member 115 is arranged in the annular groove 114. A non-microporous region of the microporous atomizing sheet 12 covers the annular groove 114. The second seal member 115 is a circular ring, and the second seal member 115 is made of rubber, silicone, or the like. The annular groove 114 is circular ring-shaped. The second seal member 115 is configured to prevent liquid pumped by the needle tube 13 from leaking out of the vaporization chamber 14, causing the precision of the vaporized dose of the medicinal liquid to be reduced. That is, the annular groove 114 is provided on the protrusion 112, and the second seal member 115 is arranged in the annular groove 114. A projection of the annular groove 114 is on a plane in which the microporous atomizing sheet 12 is located, and the annular groove 114 is arranged around the microporous region of the microporous atomizing sheet 12, that is, the inner diameter of the annular groove 114 is greater than the diameter of the microporous region.

In an embodiment, the cross section of the protrusion 112 is circular, the cross section of the opening 113 is circular, and the protrusion and the opening are concentrically arranged. The outer diameter of the annular groove 114 is equal to the inner diameter of the through hole of the central region of the piezoelectric ceramic plate of the microporous atomizing sheet 12. The second seal member 115 is arranged around the microporous region and abuts against the metal baseplate of the microporous atomizing sheet 12.

During specific implementation, the opening 113 may be a through hole or a blind hole. Specifically, the pore size of the opening 113 is greater than the outer diameter of the needle tube 13, and the end of the needle tube 13 close to the microporous atomizing sheet 12 is spaced apart from the side wall of the opening 113. In this embodiment, the opening 113 is the through hole, and the vaporization chamber 14 is an open structure, so that reversely sprayed medicinal liquid can flow out of the vaporization chamber 14 along the side wall of the vaporization chamber 14, to avoid the impact of the reversely sprayed medicinal liquid on the vaporization process. In another implementation, the opening 113 is the blind hole, and the vaporization chamber 14 is a closed structure, so that the reversely sprayed medicinal liquid can flow from the side wall of the vaporization chamber 14 to the microporous atomizing sheet 12 and finally is deposited on the bottom of the vaporization chamber 14, to avoid the impact of the reversely sprayed medicinal liquid on the vaporization process. That is, the end of the vaporization base 11 close to the microporous atomizing sheet 12 is provided with the opening 113, to enable the reversely sprayed medicinal liquid to flow to a direction away from the microporous atomizing sheet 12 along the side wall of the vaporization chamber 14 during vaporization of the microporous atomizing sheet 12, so as to prevent the reversely sprayed medicinal liquid from forming bubbles or a water film between the needle tube 13 and the microporous atomizing sheet 12 after the medicinal liquid has been vaporized, which causes the controller 31 to unable to accurately detect whether the to-be-vaporized liquid still exists and further causes the controller 31 to continue to control the microporous atomizing sheet 12 to perform vaporization, resulting in a problem of dry heating, and affecting a service life of the electronic vaporization device.

In another implementation, the pore size of the opening 113 is equal to the outer diameter of the needle tube 13, and the micro vaporization chamber 14 formed by engaging the microporous atomizing sheet 12 and the end portion of the vaporization base 11 is a closed structure and can precisely control the amount of the vaporized liquid. It may be understood that the reversely sprayed medicinal liquid cannot flow to a direction away from the microporous atomizing sheet 12 along the side wall of the vaporization chamber 14 through the micro vaporization chamber 14 of this structure, and the reversely sprayed medicinal liquid affects the vaporization process to some extent. In addition, the vaporization chamber 14 is the micro vaporization chamber 14, and the closed structure also has a probabilistic problem that the liquid is adsorbed to the bottom of the closed structure and cannot be vaporized.

Still referring to FIG. 2, the vaporization chamber 14, the needle tube 13, and the microporous region of the microporous atomizing sheet 12 are coaxially arranged. The area of a maximum cross section of the vaporization chamber 14 is less than four times the area of the microporous region of the microporous atomizing sheet 12. In this embodiment, both the cross section of the vaporization chamber 14 and the microporous region are circular, and the diameter of the vaporization chamber 14 is greater than the diameter of the microporous region and is less than the doubled diameter of the microporous region. Specifically, the diameter of the vaporization chamber 14 ranges from 4 mm to 5 mm, a distance between the end of the needle tube 13 close to the microporous atomizing sheet 12 and the side wall of the vaporization chamber 14 ranges from 1.2 mm to 1.8 mm, so that the to-be-vaporized liquid pumped by using the needle tube 13 is adsorbed between the microporous atomizing sheet 12 and the needle tube 13, for vaporizing the medicinal liquid at any angle, thereby precisely controlling the vaporized does of the medicinal liquid. If the diameter of the vaporization chamber 14 is excessively large, for example, greater than 5 mm, and the medicinal liquid adsorbed outside the microporous region is increased, an area in which the medicinal liquid is sprayed reversely is increased, the amount of reversely sprayed liquid is increased, and the precision of a dose of the medicinal liquid inhaled by the user is reduced. If the diameter of the vaporization chamber 14 is excessively small, for example, less than 4 mm, the to-be-vaporized liquid may further flow out to the side wall of the vaporization chamber in addition to being adsorbed between the microporous atomizing sheet 12 and the needle tube 13, the residual amount of unvaporized medicinal liquid is increased, and the precision of the dose of the medicinal liquid inhaled by the user is reduced.

In an embodiment, the vaporization chamber 14 is formed by using the opening 113 and the microporous atomizing sheet 12, and the diameter of the vaporization chamber 14 is the pore size of the opening 113.

A distance between the end of the needle tube 13 close to the microporous atomizing sheet 12 and the microporous atomizing sheet 12 ranges from 0.2 mm to 0.4 mm. If the distance between the end of the needle tube 13 close to the microporous atomizing sheet 12 and the microporous atomizing sheet 12 is too long, for example, greater than 0.4 mm, the amount of medicinal liquid adsorbed on the side wall of the vaporization chamber 14 is increased, a part of the medicinal liquid cannot be attached on the microporous atomizing sheet 12 and cannot be vaporized, and the precision of the dose of the medicinal liquid inhaled by the user is reduced. If the distance between the end of the needle tube 13 close to the microporous atomizing sheet 12 and the microporous atomizing sheet 12 is too short, for example, less than 0.2 mm, the medicinal liquid forms bubbles or a water film between the needle tube 13 and the microporous atomizing sheet 12 after the medicinal liquid has been vaporized. Consequently, the controller 31 cannot accurately detect whether the to-be-vaporized liquid still exists, and the controller 31 continues to control the microporous atomizing sheet 12 to perform vaporization, resulting in a problem of dry heating, and affecting a service life of the electronic vaporization device.

In an implementation, the end of the needle tube 13 close to the microporous atomizing sheet 12 is provided with a tube cover 131, and the outer wall of the tube cover 131 is spaced apart from the side wall of the vaporization chamber 14. The tube cover 131 is configured to increase the surface area of the end of the needle tube 13 close to the microporous atomizing sheet 12, that is, increase a liquid attachment area of the needle tube 13, so as to increase the adhesion of the to-be-vaporized liquid. Therefore, the to-be-vaporized liquid pumped by the needle tube 13 is better adsorbed between the end of the needle tube 13 close to the microporous atomizing sheet 12 and the microporous atomizing sheet 12. In this embodiment, the tube cover 131 is a hollow cylindrical structure, the inner diameter of the tube cover 131 is the same as the outer diameter of the needle tube 13, and the outer diameter of the tube cover is less than the diameter of the opening 113. The tube cover 131 is made of silicone, rubber, or the like. The tube cover 131 may alternatively be a solid structure, provided that the needle tube 13 is inserted into the tube cover.

The needle tube 13 is a hollow metal piece. In this embodiment, the needle tube 13 is a hollow cylindrical metal tube, the inner diameter of the needle tube 13 ranges from 0.7 mm to 1.0 mm, and the needle tube 13 is preferably made of stainless steel. The needle tube 13 may alternatively be a hollow metal piece in another structure, provided that the liquid in the liquid storage assembly 2 can be pumped to the microporous atomizing sheet 12 to form the to-be-vaporized liquid. The material of the needle tube 13 only needs to not react with the to-be-vaporized medicinal liquid and cause the medicinal liquid to deteriorate.

In an implementation, the needle tube 13 may further be configured for detection. A conductor 132 is arranged on the needle tube 13, and the conductor 132 is electrically connected to the controller 31. In this embodiment, a pogo pin is selected for the conductor 132. In another implementation, another element may alternatively be selected for the conductor 132, provided that the needle tube 13 is electrically connected to the controller 31 through the conductor 132.

The metal baseplate in the microporous atomizing sheet 12 is electrically connected to the controller 31 through a wire, the needle tube 13 is electrically connected to the controller 31 through the conductor 132 and a wire, and the needle tube 13 and the metal baseplate form an impedance sensor, that is, the needle tube 13 and the metal baseplate in the microporous atomizing sheet 12 are equivalent to two metal electrodes. After the liquid in the liquid storage assembly 2 is pumped by the needle tube 13, the to-be-vaporized liquid is adsorbed between the end of the needle tube 13 close to the microporous atomizing sheet 12 and the microporous atomizing sheet 12, to conduct the metal baseplate in the microporous atomizing sheet 12 and the needle tube 13, and a resistance value between the metal baseplate in the microporous atomizing sheet 12 and the needle tube 13 is small, about 0. After the to-be-vaporized liquid is vaporized, no to-be-vaporized liquid exists between the end of the needle tube 13 close to the microporous atomizing sheet 12 and the microporous atomizing sheet 12, the metal baseplate in the microporous atomizing sheet 12 and the needle tube 13 are in an open circuit state, and a resistance value between the metal baseplate in the microporous atomizing sheet 12 and the needle tube 13 is far greater than 0 and is also greater than the resistance value between the metal baseplate in the microporous atomizing sheet 12 and the needle tube 13 in a conduction state through the to-be-vaporized liquid.

Whether the to-be-vaporized liquid exists can be determined by detecting the resistance value between the metal baseplate in the microporous atomizing sheet 12 and the needle tube 13 by using the controller 31. That is, if the resistance value between the metal baseplate in the microporous atomizing sheet 12 and the needle tube 13 detected by the controller 31 is close to 0, it is determined that the to-be-vaporized liquid exists between the microporous atomizing sheet 12 and the needle tube 13, and the microporous atomizing sheet 12 is controlled to vaporize the to-be-vaporized liquid. If the resistance value between the metal baseplate in the microporous atomizing sheet 12 and the needle tube 13 detected by the controller 31 is far greater than 0, it is determined that the to-be-vaporized liquid between the microporous atomizing sheet 12 and the needle tube 13 is about to be consumed or has been consumed, so that the microporous atomizing sheet 12 is controlled to stop working directly or with a delay (a specific value of the delay is set according to experience, for example, 2s).

In another implementation, the needle tube 13 is made of silicone, plastic, or the like. In this case, the needle tube 13 does not have a detection function and can only be configured to pump the liquid in the liquid storage assembly 2 to the microporous atomizing sheet 12.

Due to the surface tension and the adhesion of the liquid, the liquid is adsorbed on the microporous atomizing sheet 12 after being pumped out from the needle tube 13. The liquid is located between the end of the needle tube 13 close to the microporous atomizing sheet 12 and the microporous atomizing sheet 12 and spreads around to reach the front edge of the vaporization chamber 14. During operation, the microporous atomizing sheet 12 changes the liquid into a spray, and the spray is sprayed out from the suction nozzle portion 15. During vaporization, with consumption of the liquid, under the action of atmospheric pressure, unvaporized liquid continuously moves to the microporous region of the microporous atomizing sheet 12 and is finally vaporized completely. Under the comprehensive effect of the surface tension and the adhesion of the liquid and the atmospheric pressure, the liquid conveyed by the needle tube 13 and the liquid vaporization process are completely free from the constraints of direction and gravity. Therefore, in another implementation, the needle tube 13 may alternatively be parallel to the microporous atomizing sheet 12, other structures are changed accordingly, and the working principles of the needle tube 13 and the microporous atomizing sheet 12 are the same as the foregoing. Details are not described herein again.

Figure 5:
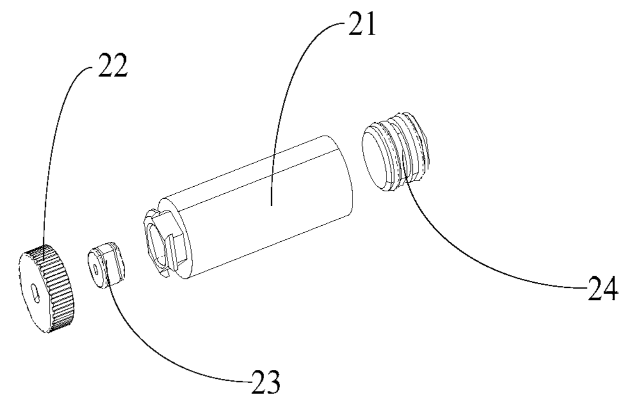
FIG. 5 is a schematic exploded view of a liquid storage assembly according to this application.

The end of the vaporization base 11 away from the microporous atomizing sheet 12 is provided with an accommodating groove 116, and the accommodating groove 116 is configured to accommodate the liquid storage assembly 2. The end of the needle tube 13 away from the microporous atomizing sheet 12 is arranged in the accommodating groove 116, to enable the end of the needle tube 13 away from the microporous atomizing sheet 12 to be inserted into the liquid storage assembly 2, so as to pump the liquid in the liquid storage assembly 2 to the microporous atomizing sheet 12. FIG. 5 is a schematic exploded view of a liquid storage assembly according to this application.

The liquid storage assembly 2 includes a liquid storage shell 21, a liquid storage cover 22, a seal plug 23, and a piston 24. One end of the liquid storage shell 21 is provided with the liquid storage cover 22, and the other end of the liquid storage shell is provided with the piston 24. One end of the liquid storage cover 22 close to the liquid storage shell 21 is provided with the seal plug 23, and the seal plug 23 is configured to seal the liquid storage shell 21, to prevent the liquid in the liquid storage assembly 2 from leaking. A space enclosed by the liquid storage shell 21, the seal plug 23, and the piston 24 together is a liquid storage tank, and the liquid storage tank is configured to store the to-be-vaporized liquid. An opening may be provided on the liquid storage cover 22, to expose a part of the seal plug 23.

The liquid storage assembly 2 is mounted in the mounting cavity 321 of the control assembly 3, and the end of the liquid storage assembly 2 provided with the seal plug 23 faces toward an opening of the mounting cavity 321, to facilitate insertion of the needle tube 13 in the vaporization assembly 1 into the liquid storage assembly 2. The end of the liquid storage assembly 2 provided with the piston 24 faces toward the bottom of the mounting cavity 321, so that a component in the control assembly 3 pushes the piston 24, to convey the liquid in the liquid storage assembly 2 to the needle tube 13, so as to reach the microporous atomizing sheet 12.

Figure 6:
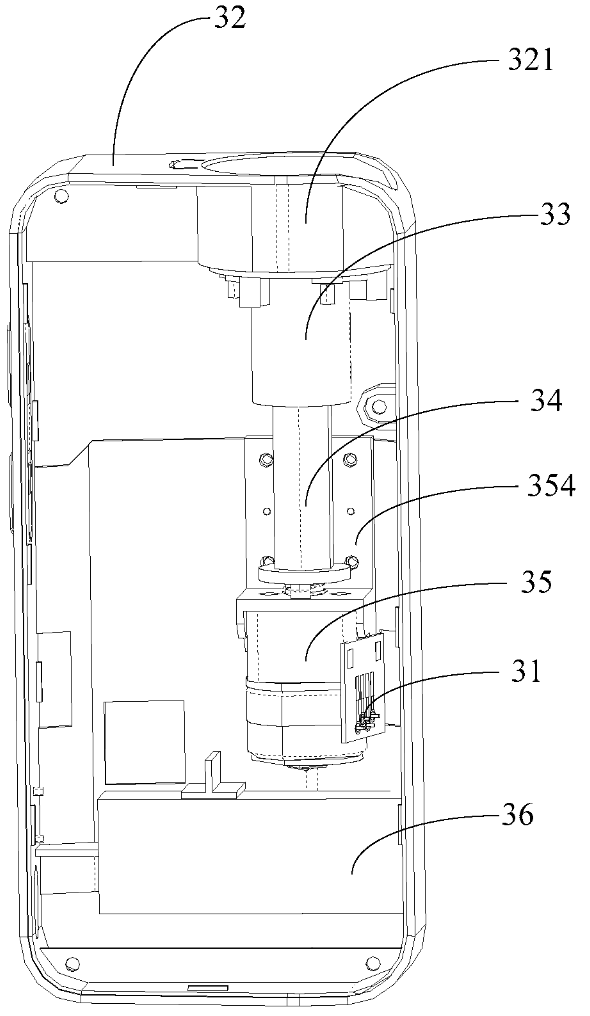
FIG. 6 is a schematic structural diagram of a first embodiment of a control assembly according to this application.

FIG. 6 is a schematic structural diagram of a first embodiment of a control assembly according to this application. The control assembly 3 further includes a control shell 32, an accommodating base 33, a push rod 34, a drive member 35, and a battery 36.

One end of the control shell 32 is provided with the mounting cavity 321, and the mounting cavity 321 is configured to accommodate the vaporization assembly 1 and a part of the liquid storage assembly 2. The part of the liquid storage assembly 2 is arranged in the accommodating groove 116 of the vaporization assembly 1 and is accommodated in the mounting cavity 321 together with the vaporization assembly 1. The structure of the mounting cavity 321 may be a ring. In this embodiment, the mounting cavity 321 is a circular ring. The mounting cavity 321 and the control shell 32 are fixed together through adhesive, bolts, or the like. Preferably, the mounting cavity 321 and the control shell 32 are integrally formed. In an embodiment, the control shell 32 includes a top wall and a bottom wall that are spaced apart from each other and an annular side wall that connects the top wall and the bottom wall. A through hole is provided at a position of the top wall close to the side wall and is used as the mounting cavity 321, and the internal space of the control shell 32 is in communication with the outside through the through hole.

The accommodating base 33 is arranged in the control shell 32 and is fixedly connected to the control shell 32.

The accommodating base 33 is arranged on one end of the mounting cavity 321 close to the bottom wall of the control shell 32, and the internal space of the accommodating base 33 is in communication with the mounting cavity 321. The accommodating base 33 and the mounting cavity 321 may be integrally formed. The accommodating base 33 is configured to accommodate the part of the liquid storage assembly 2. After the vaporization assembly 1 is inserted into the mounting cavity 321, one end of the accommodating base 33 close to the mounting cavity 321 is fixedly connected to the vaporization base 11 in the vaporization assembly 1 in a manner such as bolts, fastening, or magnetic member adsorption. In this embodiment, the end of the accommodating base close to the mounting cavity and the vaporization base are fixed through bolts. Both the end of the accommodating base 33 close to the mounting cavity 321 and one end of the vaporization base 11 close to the accommodating base 33 are provided with mounting structures (for example, mounting holes), to fix the vaporization base 11 and the accommodating base 33 together.

The push rod 34 is arranged on one end of the accommodating base 33 away from the mounting cavity 321. The push rod 34 is movably connected to the accommodating base 33, and the push rod 34 abuts against the liquid storage assembly 2 arranged in the accommodating base 33.

One end of the push rod 34 is partially accommodated in the accommodating base 33, and one end of the push rod 34 close to the drive member 35 and the drive member 35 are located outside the accommodating base.

The drive member 35 is arranged on the end of the push rod 34 away from the accommodating base 33. The drive member 35 is configured to drive the push rod 34 to move toward the liquid storage assembly 2, to enable the push rod 34 to push the piston 24 in the liquid storage assembly 2 to move toward the vaporization assembly 1, so as to convey the liquid in the liquid storage assembly 2 to the microporous atomizing sheet 12.

The battery 36 is configured to provided electric energy for operation of the microporous atomizing sheet 12 and the drive member 35. The controller 31 is configured to control working statuses of the microporous atomizing sheet 12 and the drive member 35, that is, the controller 31 controls whether the battery 36 supplies power to the microporous atomizing sheet 12 and the drive member 35. After the controller 31 controls the drive member 35 to start, the drive member 35 drives the push rod 34 to move toward the accommodating base 33, so as to convey a predetermined amount of medicinal liquid in the liquid storage assembly 2 to the vaporization chamber 14 through the needle tube 13. After detecting that to-be-vaporized medicinal liquid exists between the needle tube 13 and the microporous atomizing sheet 12 in the vaporization chamber 14, the controller 31 controls the microporous atomizing sheet 12 to perform a vaporization operation. After detecting that the medicinal liquid between the needle tube 13 and the microporous atomizing sheet 1 in the vaporization chamber 14 has been vaporized, the controller 31 controls the microporous atomizing sheet 12 to stop working. Because each moving distance of the push rod 34 may be controlled, the predetermined amount of medicinal liquid may further be controlled to be conveyed to the vaporization chamber 14 for vaporization, to precisely control the amount of vaporized liquid.

Figure 7:
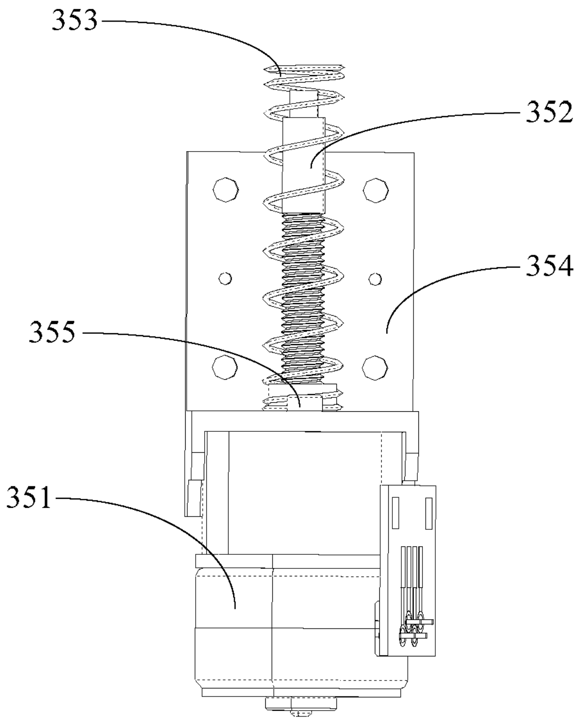
FIG. 7 is a schematic structural diagram of a drive member in a first embodiment of a control assembly according to this application.

FIG. 7 is a schematic structural diagram of a drive member in a first embodiment of a control assembly according to this application.

The drive member 35 includes a motor 351 and a screw rod 352 rotatably connected to the motor 351.

The motor 351 is fixed to the side wall of the control shell 32 by using a support element 354, and the screw rod 352 is arranged on one end of the motor 351 close to the push rod 34. That is, the motor 351 is spaced apart from the accommodating base 33. The end of the motor 351 close to the push rod 34 is provided with a first contact element 355, and the first contact element 355 is electrically connected to the controller 31. The material of the first contact element 355 may be, but not limited to, metal, provided that the first contact element can perform conduction. In this embodiment, the first contact element 355 is cylindrical.

In another implementation, the first contact element 355 may be sheet-shaped or another structure, which is designed as required.

An elastic element 353 is sleeved on the screw rod 352. In this embodiment, the elastic element 353 is a spring. In another implementation, the elastic element 353 may alternatively be another element that can be deformed and can be restored to an original state, provided that the element can meet the requirements.

In another implementation, the drive member 35 may include the motor 351 and a gear rotatably connected to the motor 351, and a tooth matching the push rod is arranged on the corresponding push rod 34, so that the drive member 35 drives the push rod 34 to move. Provided that the drive member 35 can drive the push rod 34 to move in an extending direction of the push rod. The specific structures of the drive member 35 and the push rod 34 may be designed according to requirements.

Figure 8:
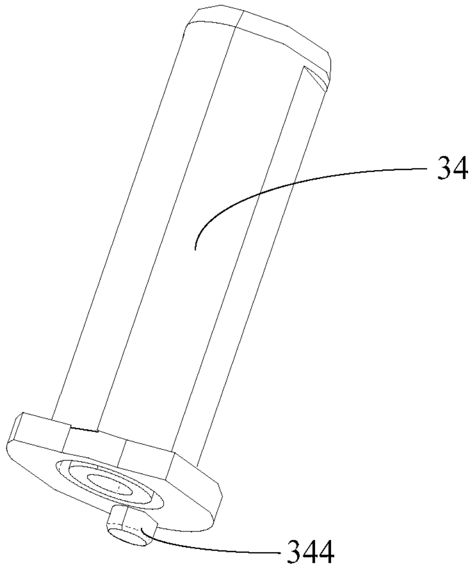
FIG. 8 is a schematic structural diagram of a push rod in a first embodiment of a control assembly according to this application.
Figure 9:
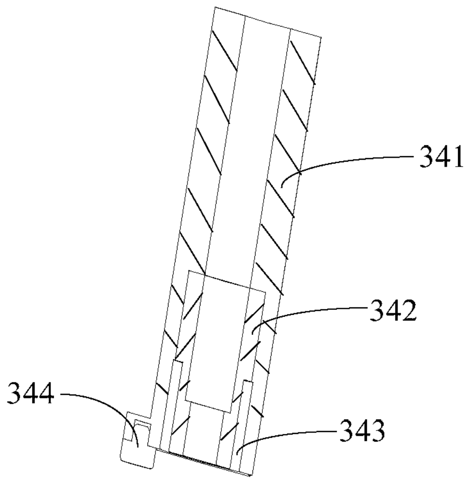
FIG. 9 is a schematic cross-sectional view of a push rod in a first embodiment of a control assembly according to this application.
Figure 10:
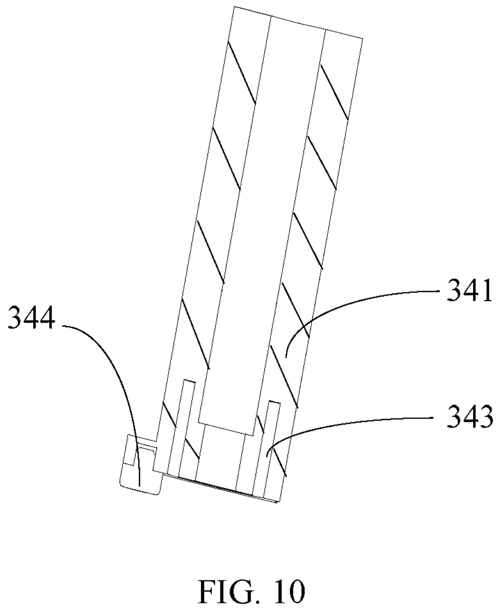
FIG. 10 is a schematic cross-sectional view of another implementation of a push rod in a first embodiment of a control assembly according to this application.

FIG. 8 is a schematic structural diagram of a push rod in a first embodiment of a control assembly according to this application. FIG. 9 is a schematic cross-sectional view of a push rod in a first embodiment of a control assembly according to this application. FIG. 10 is a schematic cross-sectional view of another implementation of a push rod in a first embodiment of a control assembly according to this application.

The end of the push rod 34 away from the accommodating base 33 is provided with a thread. The end of the push rod 34 away from the accommodating base 33 is sleeved on the screw rod 352, that is, the end of the push rod 34 provided with the thread is rotatably connected to the screw rod 352. The thread on the push rod 34 matches a thread on the screw rod 352. When the screw rod 352 rotates, the thread on the push rod 34 moves up and down along the screw rod 352. Under the drive of the screw rod 352, the push rod 34 moves toward the accommodating base 33, to push the piston 24 in the liquid storage assembly 2 to move to squeeze the medicinal liquid. A quantity of rotation circles of the screw rod 352 in a single time is controlled, so that strokes of the push rod 34 and the piston 24 are controlled, to finally achieve accurate liquid feeding.

To precisely control the amount of liquid pumped out from the liquid in the liquid storage assembly 2 by using the needle tube 13, the precision of the thread on the screw rod 352 and the precision of the thread on the push rod 34 are set to be less than or equal to level 5, to improve the precision of a single rotation and to precisely control the moving distance of the push rod 34, thereby precisely controlling the vaporized dose. It may be understood that the selection of the thread precision is also associated with a requirement of vaporization precision, higher precision indicates higher vaporization precision, and a smaller value set for the thread precision indicates higher precision.

In this embodiment, as shown in FIG. 9, the push rod 34 includes a push rod body 341 and a nut 342, and the nut 342 is arranged on the end of the push rod 34 away from the accommodating base 33 and is arranged on the inner wall of the push rod body 341. In another implementation, as shown in FIG. 10, the push rod 34 includes the push rod body 341 and a thread formed on the inner wall of the push rod body 341, and the thread is arranged on the end of the push rod body 341 away from the accommodating base 33.

One end of the push rod body 341 close to the drive member 35 is provided with a limiting groove 343, and the limiting groove 343 is provided around the thread on the push rod body 341. The limiting groove 343 is configured to accommodate the elastic element 353 sleeved on the screw rod 352. When the push rod 34 is sleeved on the screw rod 352, one end of the elastic element 353 abuts against the bottom wall of the limiting groove 343, and the other end of the elastic element abuts against the motor 351. With the rotation of the screw rod 352, the elastic element 353 is compressed, the elastic element 353 applies a force that is opposite to a moving direction of the push rod to the push rod 34, to eliminate a gap between the thread on the screw rod 352 and the thread on the push rod 34, so that the thread on the screw rod 352 matches the thread on the push rod 34 more closely, to precisely control the moving distance of the push rod 34. In another implementation, the elastic element 353 is fixedly connected to the motor 351, to eliminate the gap between the thread on the screw rod 352 and the thread on the push rod 34.

The end of the push rod 34 close to the drive member 35 is provided with a second contact element 344, and the second contact element 344 is electrically connected to the controller 31. A material of the second contact element 344 may be, but not limited to, metal, provided that the second contact element can perform conduction. In this embodiment, the second contact element 344 is cylindrical. A sum of the height after the first contact element 355 abuts against the second contact element 344 and the depth of the limiting groove 343 is the same as the height of the elastic element 353 after being compressed to the greatest extent. In another implementation, the second contact element 344 may be sheet-shaped or another structure, which may be designed as required.

When the screw rod 352 drives the push rod 34 to move away from the accommodating base 33, that is, drives the push rod 34 to move toward the motor 351, and after the first contact element 355 is in contact with the second contact element 344, the controller 31 detects that the first contact element 355 is conducted to the second contact element 344 and controls the motor 351 to stop rotating, so that the push rod 34 stops moving toward the motor 351, to restrict a downward movement position of the push rod 34.

Figure 11:
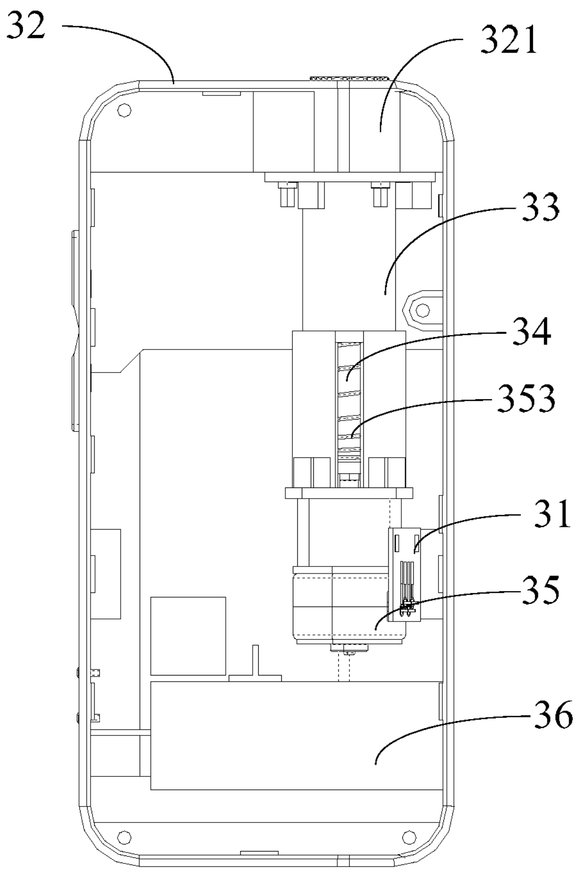
FIG. 11 is a schematic structural diagram of a second embodiment of a control assembly according to this application.
Figure 12:
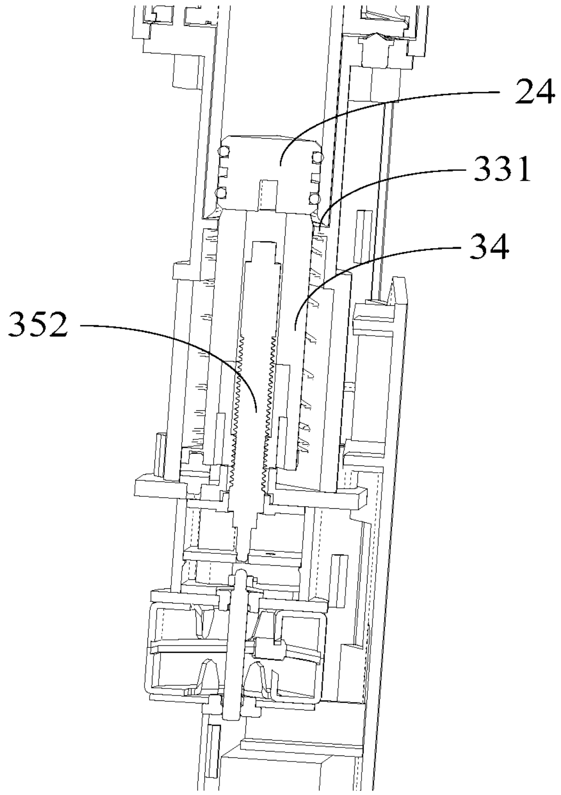
FIG. 12 is a schematic cross-sectional view of a second embodiment of a control assembly according to this application.
Figure 13:
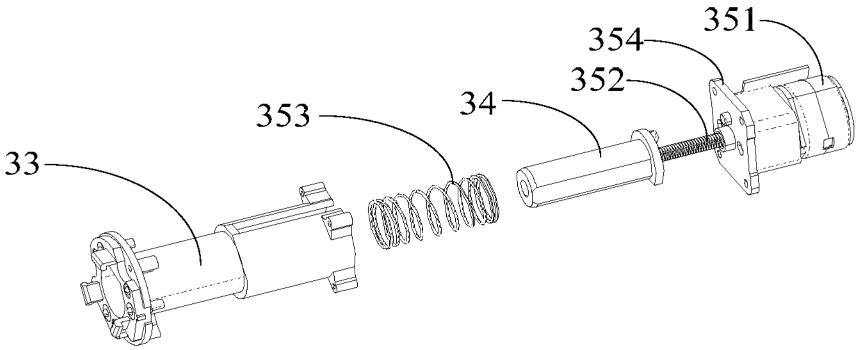
FIG. 13 is a schematic exploded view of a second embodiment of a control assembly according to this application.

FIG. 11 is a schematic structural diagram of a second embodiment of a control assembly according to this application. FIG. 12 is a schematic cross-sectional view of a second embodiment of a control assembly according to this application. FIG. 13 is a schematic exploded view of a second embodiment of a control assembly according to this application.

In the second embodiment, the structure of the control assembly 3 is substantially the same as that in the first embodiment, except that the structure of the accommodating base 33, the arrangement position of the elastic element 353, and the connection relationship between the accommodating base 33 and the push rod 34 as well as the drive member 35.

In this embodiment, the accommodating base 33, the push rod 34, and the drive member 35 are of an integral structure. One end of the accommodating base 33 is fixed to the mounting cavity 321 and is in communication with the mounting cavity 321. The other end of the accommodating base 33 is fixed to the support element 354. A part of the liquid storage assembly 2 is accommodated in the accommodating base 33. The push rod 34 and the screw rod 352 of the drive member 35 are arranged in the accommodating base 33 as a whole. The motor 351 is arranged on a side of the support element 354 away from the accommodating base 33, and the accommodating base 33 is fixedly connected to the motor 351 by the support element 354. It may be understood that to improve the precision of the vaporized dose, the rigidity of the entire structure, that is, the ability not to deform, needs to be improved, that is, it is expected that the position of the push rod 34 does not change due to another factor during rotation of the screw rod 352. The accommodating base 33, the push rod 34, and the drive member 35 are set to an integral structure, which can prevent the support element 354 of the drive member 35 from being slightly deformed in the moving direction of the push rod 34 when the screw rod 352 drives the push rod 34 to move, causing the thrust of the motor 351 to be offset. The accommodating base 33 is fixedly connected to the support element 354, and the accommodating base 33 is fixed to the control shell 32, to prevent the support element 354 from being deformed, thereby improving the precision of the vaporized dose.

A limiting element 331 is arranged in the accommodating base 33, and the limiting element 331 is an annular structure and is arranged on the inner wall of the accommodating base 33. The limiting element 331 may be fixedly connected to the accommodating base 33 through adhesive or the like. Preferably, the limiting element 331 and the accommodating base 33 are integrally formed. The limiting element 331 is arranged on one end of the liquid storage assembly 2 close to the drive member 35 and abuts against the liquid storage assembly 2. That is, the limiting element 331 is arranged on the end of the push rod 34 close to the liquid storage assembly 2.

The limiting element 331 is configured to prevent the push rod 34 from rotating with the rotation of the screw rod 352, that is, to limit shaking of the push rod 34. A gap between the push rod 34 and the limiting element 331 is controlled within 0.05 mm, to prevent the push rod 34 from shaking to the greatest extent, and to precisely control the moving distance of the push rod 34, thereby precisely controlling the vaporized dose.

The elastic element 353 is sleeved on the push rod 34, that is, the push rod 34 is elastically connected to the accommodating base 33.

In this embodiment, the elastic element 353 is a spring, one end of the spring abuts against the limiting element 331, and the other end of the spring is fixed to a flange of the outer wall of one end of the push rod 34 close to the motor 351. With the rotation of the screw rod 352, the push rod 34 moves toward the piston 24, the elastic element 353 is compressed, the elastic element 353 applies a force that is opposite to a moving direction of the push rod to the push rod 34, to eliminate a gap between the thread on the screw rod 352 and the thread on the push rod 34, so that the thread on the screw rod 352 matches the thread on the push rod 34 more closely, and the push rod 34 does not shake, to precisely control the moving distance of the push rod 34. In another implementation, the elastic element 353 may alternatively be another element that can be deformed and can be restored to an original state, provided that the element meets the requirements.

The electronic vaporization device in this application includes a microporous atomizing sheet and a needle tube, where one end of the needle tube is spaced apart from the microporous atomizing sheet, and the other end of the needle tube is configured for insertion into a liquid storage assembly; and the needle tube is configured to convey liquid in the liquid storage assembly to the microporous atomizing sheet to form to-be-vaporized liquid; and the microporous atomizing sheet is configured to vaporize the to-be-vaporized liquid, and the to-be-vaporized liquid is adsorbed between the microporous atomizing sheet and the needle tube through surface tension. Liquid in the liquid storage assembly is conveyed to the microporous atomizing sheet by using the needle tube, to precisely control the vaporized dose, which can prevent a patient from inhaling excessive medicinal liquid or insufficient medicinal liquid, thereby achieving an expected therapeutic effect for a vaporization inhalation therapy.

The foregoing descriptions are merely some embodiments of this application, and the protection scope of this application is not limited thereto. All equivalent apparatus or process changes made according to the content of this specification and accompanying drawings in this application or by directly or indirectly applying this application in other related technical fields shall fall within the protection scope of this application.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article “a” or “the” in introducing an element should not be interpreted as being exclusive of a plurality of elements. Likewise, the recitation of “or” should be interpreted as being inclusive, such that the recitation of “A or B” is not exclusive of “A and B,” unless it is clear from the context or the foregoing description that only one of A and B is intended. Further, the recitation of “at least one of A, B and C” should be interpreted as one or more of a group of elements consisting of A, B and C, and should not be interpreted as requiring at least one of each of the listed elements A, B and C, regardless of whether A, B and C are related as categories or otherwise. Moreover, the recitation of “A, B and/or C” or “at least one of A, B or C” should be interpreted as including any singular entity from the listed elements, e.g., A, any subset from the listed elements, e.g., A and B, or the entire list of elements A, B and C.

What is claimed is:

1. An electronic vaporization device, comprising:

a microporous atomizing sheet; and a needle tube, one end of the needle tube being spaced apart from the microporous atomizing sheet, and an other end of the needle tube being configured for insertion into a liquid storage assembly, the needle tube being configured to convey liquid in the liquid storage assembly to the microporous atomizing sheet to form to-be-vaporized liquid, the to-be-vaporized liquid being adsorbed between the microporous atomizing sheet and the needle tube through surface tension, wherein a tube cover is arranged on the end of the needle tube that is spaced apart from the microporous atomizing sheet. a peripheral surface of the needle tube and a peripheral surface of the tube cover being flush and extending radially outward so as to increase adhesion of the to-be-vaporized liquid.

2. The electronic vaporization device of claim 1, further comprising:

a vaporization base, wherein the microporous atomizing sheet is arranged on one end of the vaporization base and is engaged with an end portion of the vaporization base to form a vaporization chamber, wherein the needle tube is fixed to the vaporization base, and wherein the end of the needle tube that is spaced apart from the microporous atomizing sheet is arranged in the vaporization chamber.

3. The electronic vaporization device of claim 2, wherein the microporous atomizing sheet comprises a microporous region, wherein both a cross section of the vaporization chamber and the microporous region are circular, and wherein the vaporization chamber, the microporous region of the microporous atomizing sheet, and the needle tube are coaxially arranged.

4. The electronic vaporization device of claim 3, wherein a diameter of the vaporization chamber is greater than a diameter of the microporous region and is less than a doubled diameter of the microporous region.

5. The electronic vaporization device of claim 3, wherein a diameter of the vaporization chamber ranges from 4 mm to 5 mm, and wherein a distance between the end of the needle tube that is spaced apart from the microporous atomizing sheet and a side wall of the vaporization chamber ranges from 1.2 mm to 1.8 mm.

6. The electronic vaporization device of claim 3, wherein a distance between the end of the needle tube that is spaced apart from the microporous atomizing sheet and the microporous atomizing sheet ranges from 0.2 mm to 0.4 mm.

7. The electronic vaporization device of claim 2, wherein an end of the vaporization base close to the microporous atomizing sheet is provided with an annular groove, and a seal member is arranged in the annular groove, and wherein a non-microporous region of the microporous atomizing sheet covers the annular groove.

8. The electronic vaporization device of claim 7, wherein the annular groove is circular ring-shaped, the seal member comprises a circular ring, and the seal member comprises silicone.

9. The electronic vaporization device of claim 2, wherein the end of the vaporization base on which the microporous atomizing sheet is arranged is provided with an opening, wherein the microporous atomizing sheet covers the opening and is engaged with the opening to form the vaporization chamber, and wherein the end of the needle tube that is spaced apart from the microporous atomizing sheet is spaced apart from a side wall of the opening.

10. The electronic vaporization device of claim 9, wherein the opening is a through hole or a blind hole.

11. The electronic vaporization device of claim 2, wherein an end portion of the vaporization base away from the microporous atomizing sheet is provided with an accommodating groove configured to accommodate the liquid storage assembly, and wherein an end of the needle tube away from the microporous atomizing sheet is arranged in the accommodating groove.

12. The electronic vaporization device of claim 2, wherein at least a portion of the tube cover extends within the vaporization chamber, the portion of the tube cover extending within the vaporization chamber extending along a first axial length of the tube cover, wherein the first axial length and a second axial length form a total axial length of the tube cover, and wherein the first axial length is greater than the second axial length.

13. The electronic vaporization device of claim 1, wherein an outer wall of the tube cover is spaced apart from a side wall of the vaporization chamber, and wherein the tube cover comprises silicone.

14. The electronic vaporization device of claim 1, wherein the needle tube comprises a hollow cylindrical metal tube, and an inner diameter of the needle tube ranges from 0.7 mm to 1.0 mm.

15. The electronic vaporization device of claim 14, further comprising:

a controller, wherein a conductor is arranged on the needle tube, and the conductor is electrically connected to the controller, wherein the microporous atomizing sheet is electrically connected to the controller, and the needle tube and the microporous atomizing sheet form an impedance sensor, and wherein the controller is configured to detect a resistance value between the needle tube and the microporous atomizing sheet and to control an operating state of the microporous atomizing sheet according to a detection result.

16. The electronic vaporization device of claim 1, wherein the tube cover is a hollow cylinder with uniform thickness along its entire axial length.

17. The electronic vaporization device of claim 1, wherein the tube cover and the needle tube extend in an axial direction, and wherein the peripheral surface of the tube cover and the peripheral surface of the needle tube extend perpendicular to the axial direction.

* * * * *